United States Patent [19]

Stanley et al.

[11] 4,069,106

[45] Jan. 17, 1978

[54] IMMOBILIZATION OF ENZYMES ON KERATIN

[75] Inventors: William L. Stanley, El Cerrito; Glenn G. Watters; Bock G. Chan, both of Albany, all of Calif.

[73] Assignee: The United States of America as represented by the Secretary of Agriculture, Washington, D.C.

[21] Appl. No.: 758,897

[22] Filed: Jan. 13, 1977

[51] Int. Cl.$^2$ .......................... C07G 7/02; G01N 31/14
[52] U.S. Cl. ........................................ 195/68; 195/63; 195/DIG. 11; 195/103.5 U
[58] Field of Search .................... 195/63, 68, DIG. 11, 195/103.5 U

[56] References Cited

U.S. PATENT DOCUMENTS

| 2,474,339 | 6/1949 | Ward et al. | 195/113 X |
| 3,977,941 | 8/1976 | Vieth et al. | 195/68 X |

OTHER PUBLICATIONS

Axen et al., The Use of Isocyanides for the Attachment of Biologically Active Substances to Polymers, Acta Chemia Scandinavica, vol. 25, 1971, (pp. 1129–1169).

*Primary Examiner*—David M. Naff
*Attorney, Agent, or Firm*—M. Howard Silverstein; David G. McConnell; Theodore J. Leitereg

[57] ABSTRACT

Insolubilized but active enzymes are prepared by mixing an aqueous solution of the enzyme with reduced keratin-containing material. The invention is particularly useful for insolubilizing sulfhydryl-containing enzymes such as urease.

1 Claim, No Drawings

IMMOBILIZATION OF ENZYMES ON KERATIN

BACKGROUND OF THE INVENTION

1. Field of the Invention

This invention relates to and has among its objects the provision of novel water-insoluble but active enzyme products and methods for preparing them. Further objects of the invention will be evident from the following description wherein parts and percentages are by weight unless otherwise specified.

2. Description of the Prior Art

In recent years there has been considerable interest in preparing enzymes in insolubilized (sometimes referred to as immobilized) form. Such products enable enzyme-catalyzed reactions to be carried out in a simplified and efficient manner. Typically, the insolubilized enzyme is placed in a cylindrical vessel and a solution of the substrate to be reacted is passed through the enzyme column. The reaction takes place within the column and the effluent liquor contains the reaction products. With this system the enzyme can be used repeatedly for processing fresh batches of the substrate. Various techniques have been advocated for preparing insolubilized enzymes. One procedure is to entrap the enzyme in polymerizing polyacrylamide; another is to adsorb it on insoluble media such as ion exchange resins, alumina, etc.

Difficulty, however, has been encountered in preparing immobilized sulfhydryl-containing enzymes such as urease. Chemical cross-linking agents have a deleterious effect on the enzyme. For example, attempts at insolubilizing urease with such conventional agents as glutaraldehyde, cyanogen bromide, and substituted agarose gels were unsuccessful in that they substantially reduced the urease activity.

SUMMARY OF THE INVENTION

In accordance with the invention, insolubilized but active enzymes are prepared from enzymes which are in a normal or native (soluble) state. A water solution of the enzyme is mixed with keratin-containing material which is first pretreated with a reducing agent. The enzyme becomes immobilized on the reduced keratin and the product is ready for use.

The invention provides many important advantages, typical examples of which are outlined below.

A primary advantage of the products of the invention is that their activity is retained over long periods of use. Thus, the products of the invention have the advantage not only of being reusable, but also usable under conditions of continuous operation for long periods of time and with large amounts of substrates.

Another advantage of the invention is that the keratin not only contributes to insolubilization of the enzyme applied thereto, but also provides useful physical properties to the product. In particular, the keratin acts as a support or carrier so that the insolubilized enzyme product forms a column through which water and other liquids can percolate readily. This is in shape contrast to known insolubilized enzymes many of which are generally amorphous materials that cannot be used directly in a column because liquids will not flow therethrough. These known products require the addition of a carrier such as diatomaceous earth, crushed firebrick, or the like to provide a liquid-permeable mass.

Another advantage of the invention is that the products are afforded by simple procedures using readily-available reactants. No exotic chemicals or complicated procedures are required. Nonetheless, the products retain a significant and sufficient part of the activity of the starting enzyme. In some cases, the major part of the original activity is retained.

A further advantage of the invention is that useful products can be prepared from any enzyme source, including pure enzymes, enzyme concentrates, crude enzyme preparations, and even such substances as animal organs, plant parts, microbial cultures, and the like. Important in this regard is that application of the herein-described reactants causes most of the active enzyme to be selectively precipitated even where it is present in minute quantity, e.g., as little as 1 mg. of active enzyme in association with gram quantities of inactive components. Accordingly, the invention provides the means for preparing insolubilized products from enzymes which previously were difficult to insolubilize or which were never insolubilized.

Another advantage of the invention lies in the precise control that one can excercise over the extent and direction of enzymic reactions. This results because of the solid nature of the products of the invention which allows specific amounts to be metered out to suit any particular situation.

Another advantage of the invention is that enzymic reactions can be stopped at any desired time by simply separating the solution under treatment from the insolubilized enzyme—for example, by draining the solution away from the reaction system. Thus, no external forces—such as heat, acid, and the like which might be detrimental—need by applied to short-stop the reaction.

Another advantage of the invention is that keratin is waste material and therefore is inexpensive and available in large quantities. Thus the products of the invention can be produced more economically than where known insolubilizing agents are used.

A most important advantage of the invention is that no crosslinking agent is used. The enzyme is reacted directly with the reduced keratin to produce the insolubilized enzyme product. Consequently, the activity of the enzyme is not destroyed or appreciably decreased.

DESCRIPTION OF THE PREFERRED EMBODIMENTS

Preparation of the products of the invention involves reaction of reduced keratin with the enzyme. Reduced keratin is prepared by treating keratin-containing material with a reducing agent. Preferably, the procedure outlined in U.S. Pat. No. 2,474,339 is followed. The keratin is dissolved in an aqueous alcoholic (ethanol, propanol, and the like) solution containing 0.25 to 3.0 parts of alcohol per part of water (volume to volume). Additionally, the aqueous alcoholic solution contains about 1 to 10%, based on the amount of keratin material, of a sulfur-containing, reductive disulphide-splitting agent, such as mercaptoethanol. The temperature of the reduction reaction is about 50° to 110° C. and the duration of contact is about 20 to 80 minutes. Water is added gradually to the alcoholic solution to precipitate the reduced keratin in a granular form. Usually, about 0.5 to 3 parts of water are used per part of alcoholic solution. During this precipitation it is desirable to vigorously agitate the material; thus, the solution should be stirred, shaken, rocked, etc., during the addition of water to achieve this agitation. It may be necessary to break up larger pieces of the granular product to pass through a 20 to 80 mesh screen. The product is washed thoroughly with water and collected by filtration, decantation, centrifugation, and the like. The so-prepared reduced keratin is now ready for reaction with an enzyme.

Alternatively and preferably, precipitation of the reduced keratin in granular form may be accomplished by cooling the above hot alcoholic solution slowly with gentle agitation. In general, the hot alcoholic solution should be cooled to ambient temperature over a period of 1 to 2 hours. The so-precipitated material can then be treated as described above.

It should be noted that other methods for reducing the disulphide linkage in the keratin-containing material may be used without departing from the scope of the invention.

The keratin-containing material used in the invention can be selected from a wide variety of sources, namely, poultry feathers, cattle hoof, hog hoof, animal hair, animal horn, animal hide, snake skin, etc.

Next, the enzyme to be insolubilized is dissolved in distilled water. Where necessary, the pH of the water is adjusted by conventional methods to a level at which the enzyme is soluble. Appropriate pH's to use with any particular enzyme are described in the literature. In most cases the pH selected will be about 3 to 7. It may further be noted that oftentimes the starting material already contains a buffer or other pH-adjusting agent so that when it is mixed with water the resulting dispersion will exhibit a pH at which the enzyme is most soluble. This is particularly the case with commercially-available enzyme preparations. It is obvious that in such cases there is no need to apply any pH adjustment.

Following preparation of the aqueous solution of the starting material, a mechanical separation step such as filtration or decantation can be applied to remove fillers, debris, or other undissolved material. It may also be necessary to add to the aqueous enzyme dispersion, minor amounts of purifying agents such as potassium chloride, sodium ethylene diamine tetraacetate, etc., to remove impurities such as inactive proteins and heavy metal ions which might be detrimental to the activity of the enzyme in later reactions.

The aqueous dispersion of the starting enzyme is added to the reduced keratin. Generally, about 0.01 to 1 parts of crude enzyme per 10 parts of reduced keratin are used. The mixture is gently agitated by conventional means such as shaking, stirring, or the like while being held for 1 to 48 hours at a temperature of about 1° to 25° C. in order to cause the enzyme to react with the reduced keratin.

It is within the compass of the invention to place the reduced keratin material in a column and to percolate or pump the aqueous enzyme solution therethrough. The enzyme becomes immobilized on the reduced keratin and the column is then ready for use in enzymic reactions.

The invention is of wide versatility and can be applied to all kinds of enzymes which contain sulfhydryl groups. Illustrative examples are urease, papain, yeast alcohol dehydrogenase, aspartate kinase, phosphofructokinase, carbamyl phosphate synthetase, fructose diphosphatase, ribulose diphosphate carboxylase, citrate cleavage enzyme, methionine-S-$RN_4$ synthetase, and the like. The starting enzyme need not be a purified substance but may be a preparation containing an enzyme. Thus, for example, one may employ microbial preparations which contain enzymes, typically, cultures or cells of yeasts, molds, bacteria, and the like. Other enzyme-containing preparations which may be applied to the process of the invention are such materials as animal organs, e.g., pancreas, liver, etc., insects and insect parts, barley malt, pineapple, papaya, etc.

The products of the invention can be utilized in a variety of ways. An example is provided below by way of illustration and not limitation.

Urease is immobilized on reduced poultry feather keratin by the procedure described hereinabove. The isolubilized enzyme is packed into a column which can be used in clinical analysis procedures. Urea solutions are percolated through the column and the urea is decomposed into ammonia and carbon dioxide by the action of the immobilized urease.

It is believed that formation of the products of the invention involves reaction between the sulfhydryl groups of the enzyme with those of the reduced keratin-containing material. In this way, the enzyme becomes chemically bonded to a rigid backbone. However, it is not meant to limit the invention to a particular mode of action.

EXAMPLE

The invention is further demonstrated by the following illustrative example.

Preparation of Urease Immobilized on Poultry Feather Keratin

Powdered poultry feathers (2 g.) were suspended in 100 ml. of 50% aqueous 2-propanol solution and mercaptoethanol was added until the concentration thereof was 2% by volume. The mixture was heated to 80° C. with gentle stirring and held at that temperature for 30 minutes. Undissolved material was removed by filtering the solution through a glass wool on a heated funnel. The opaque filtrate was allowed to cool to ambient temperature over a period of 1 hour with constant, gentle mechanical stirring. The reduced keratin precipitated in granular form, and the precipitate was washed with water and collected by filtration. Larger pieces were broken up to pass through a 20-mesh screen.

A 15-gram portion of the reduced keratin was packed with light tamping into a column 1.2 cm. in diameter and 18 cm. in length.

A solution of 150 mg. of urease in 50 ml. of distilled water was prepared. The solution was made $10^{-3}$ M in sodium ethylene diamine tetracetate. The mixture was centrifuged at 12,000 g. for 20 min. and the precipitate was discarded.

The supernatant solution (UV absorbance of 1.6 at 260 nm.) was pumped through the above column until 30 ml. (over one bed volume) thereof had been used. The UV absorbance of the eluate was 1.3 at 260 nm. The column was washed with 50 ml. of 0.1 M potassium chloride solution containing $10^{-3}$ M sodium ethylene diamine tetraacetate.

An aqueous urea solution (0.2 M in urea and $10^{-3}$ M in sodium ethylene diamine tetraacetate) was passed through the column at room temperature at a rate of 60 ml. per hour. Five-ml. eluate fractions were collected. The extent of urea hydrolysis was determined by analyzing 1- or 2-ml. aliquots of each fraction for ammonia with an automatic titrimeter. The results are summarized below:

| Eluate fraction | 1 | 2 | 3 | 4 | 5 | 6 | 7 | 8 | 9 | 10 |
|---|---|---|---|---|---|---|---|---|---|---|
| Hydrolysis, % | 2.7 | 25.7 | 79 | 85 | 73 | 67 | 63 | 62.5 | 57 | 57.5 |

| Eluate fraction | 11 | 12 | 13 | 14 | 15 |
|---|---|---|---|---|---|
| Hydrolysis, % | 59 | 55 | 53 | 53 | 59 |

Having thus described our invention, we claim:

1. A process for preparing an insoluble but active enzyme, which comprises —
   a. reacting keratin-containing material with a sulfur-containing, reductive, disulphide-splitting agent to reduce keratin and produce a reduced keratin-containing material,
   b. dissolving a soluble sulfhydryl group containing enzyme in water, and
   c. mixing said reduced keratin-containing material with the solution of the enzyme in water so that the enzyme reacts directly with the reduced keratin and becomes chemically bonded to said reduced keratin-containing material.

* * * * *